United States Patent
Trent et al.

(10) Patent No.: US 10,151,635 B1
(45) Date of Patent: Dec. 11, 2018

(54) REAL TIME CORRECTION OF OPTICAL WINDOW THERMAL GRADIENTS

(71) Applicant: Raytheon Company, Waltham, MA (US)

(72) Inventors: Catherine Trent, Allen, TX (US); Gary A. Frazier, Garland, TX (US); David J. Knapp, Tucson, AZ (US)

(73) Assignee: RAYTHEON COMPANY, Waltham, MA (US)

( * ) Notice: Subject to any disclaimer, the term of this patent is extended or adjusted under 35 U.S.C. 154(b) by 2 days.

(21) Appl. No.: 15/617,163

(22) Filed: Jun. 8, 2017

(51) Int. Cl.
*G01J 5/00* (2006.01)
*G01N 21/41* (2006.01)
*G01N 21/17* (2006.01)

(52) U.S. Cl.
CPC ............ *G01J 5/0022* (2013.01); *G01N 21/41* (2013.01); *G01J 2005/0029* (2013.01); *G01J 2005/0077* (2013.01); *G01J 2005/0085* (2013.01); *G01N 2021/1731* (2013.01)

(58) Field of Classification Search
CPC . G01J 5/0022; G01J 2005/0029; G01N 21/41
See application file for complete search history.

(56) References Cited

U.S. PATENT DOCUMENTS

| 5,400,161 | A | 3/1995 | Lambert, Jr. | |
|---|---|---|---|---|
| 6,552,318 | B1 * | 4/2003 | Crowther | F41G 7/2213 250/201.9 |
| 9,146,437 | B2 | 9/2015 | Driscoll et al. | |
| 2004/0211892 | A1 * | 10/2004 | Stallard | G02B 7/028 250/239 |

FOREIGN PATENT DOCUMENTS

WO    1999/018468 A1    4/1999

OTHER PUBLICATIONS

International Search Report and Written Opinion for corresponding International Search Report PCT/US2018/017897 dated May 9, 2018.
Dong et al., "Dynamic Aberration Correction for Conformal Window of High-Speed Aircraft Using Optimized Model-Based Wavefront Sensorless Adaptive Optics", Sensors, vol. 16, No. 9, Sep. 2, 2016, pp. 1-13.

* cited by examiner

*Primary Examiner* — Hugh H Maupin
(74) *Attorney, Agent, or Firm* — Renner, Otto, Boisselle & Sklar, LLP

(57) ABSTRACT

A thermal detection system for detecting a thermal profile of an optical window may be used in an airborne body that contains a sensor system. The system may include a thermal imager arranged within the airborne body for imaging a portion of the optical window and the portion may coincide with an optical path of the sensor system. The system may further include a processor in communication with the thermal imager for receiving images of the portion and determining a thermal gradient of the portion. The processor may be configured to apply corrections to active optical elements of the sensor system to accommodate for adverse thermal effects on the optical sensor that interferes with the sensor system performance.

20 Claims, 4 Drawing Sheets

REAL TIME CORRECTION OF OPTICAL WINDOW THERMAL GRADIENTS

FIELD OF THE INVENTION

The invention relates to a system and method for measuring the thermal profile of an airborne optical window in real-time, and more particularly to measuring the thermal profile of the window and applying corrections to an optical system to accommodate for thermal distortions of the window that impact the performance of the optical system.

DESCRIPTION OF THE RELATED ART

Optical windows may be used in a variety of applications, such as in defense type applications that use airborne vehicles. Examples of airborne vehicles include missiles, aircrafts, and spaceplanes, or other vehicles that may be used to execute a mission. The airborne vehicle may include a sensor system that is located within the main body of the vehicle for performing various functions. The vehicle generally includes a radome or optical window that surrounds the sensor system. The sensor performance may rely on optical rays that enter and exit through the optical window. During flight of the vehicle, the optical window is generally subject to mechanical and thermal stresses and a thermal gradient may be produced across the window. The resulting thermal gradient may change an optical index of refraction and optical absorption coefficients of the window materials such that the normal paths of the optical rays may be distorted. Thus, the thermal distortion may cause a reduction in sensor performance and impact the normal vehicle functions.

Determining the thermal gradient is advantageous in that the thermal gradient may be used to apply corrections to optical elements of the sensor system and accommodate for the thermal gradient. Conventionally, one method used to determine the thermal gradient includes storing and using a lookup table to estimate an index of refraction change due to temperature based upon current conditions of the vehicle, such as speed, altitude, and environmental conditions. However, using a lookup table may be disadvantageous in that the aero effects are not directly measured in real-time and the thermal gradient may not be precisely determined.

Another method for determining the thermal gradient includes using thermocouples that are integrated in the optical window itself. However, using thermocouples may be disadvantageous due to thermocouples reducing transparency of the optical window, causing scatter, and increasing the complexity of the window configuration. Additionally, thermocouples are generally suited for flat-shaped windows and may be inadequate for windows having more complex and conformal geometries.

SUMMARY OF THE INVENTION

A thermal imager may be used to image an optical window from inside the window. The thermal imager may be configured to determine a real-time temperature profile of the optical window. The thermal imager may send thermal images to a processor and the processor may convert the images into a thermal gradient map. The processor may use the thermal gradient map to determine a wavefront error of a sensor system contained within the optical window. The processor may be in communication with an optical corrector such that corrections may be applied to active optical elements of the sensor system to accommodate for the wavefront error.

The following aspects of the invention may be combinable in any combination.

According to an aspect of the invention, a thermal detection system for detecting a thermal profile of an optical window may be used in an airborne body that contains a sensor system. The thermal detection system may include a thermal imager arranged within the airborne body that images a portion of the optical window. The portion may coincide with an optical path of the sensor system. The thermal detection system may include a processor in communication with the thermal imager that receives images of the portion of the optical window and determines a thermal gradient of the portion. The processor may be configured to apply corrections to active optical elements of the sensor system.

According to an aspect of the invention, the thermal detection system may include a mid-wave infrared sensor or a long-wave infrared sensor.

According to an aspect of the invention, the thermal imager may include a microbolometer.

According to an aspect of the invention, the thermal imager may include a visible camera.

According to an aspect of the invention, an airborne body may include an optical system and the optical system may include an optical window, an optical sensor that is operable along an optical axis, a thermal imager that images an interior area of the optical window, a processor, and an optical corrector. The interior area may coincide with the optical axis. The processor may be in communication with the thermal imager and receives images of the interior area and determines a thermal gradient of the predetermined interior area. The optical corrector may be in communication with the processor and use the thermal gradient to apply corrections to the optical sensor to accommodate for adverse thermal effects on the optical sensor.

According to an aspect of the invention, the thermal imager may be arranged offset to the optical axis of the optical sensor.

According to an aspect of the invention, the optical window may be formed of a transparent material having a transmissivity band in a mid-wave infrared range.

According to an aspect of the invention, the optical window may be formed of an opaque material having a transmissivity band in a long-wave infrared range.

According to an aspect of the invention, the thermal imager may include a microbolometer.

According to an aspect of the invention, the optical sensor is a long-wave infrared sensor and the long-wave infrared sensor may be used as the thermal imager.

According to an aspect of the invention, the thermal imager may include a visible camera.

According to an aspect of the invention, the thermal imager may include a long-wave infrared sensor.

According to an aspect of the invention, the optical window may be a radome or a conformal dome.

According to an aspect of the invention, a method for detecting a thermal profile of an optical window may be used in an airborne vehicle that contains a sensor system. The method may include imaging a portion of the optical window that coincides with an optical path of the sensor system, determining the thermal gradient of the portion of the optical window, and applying corrections to optical elements of the sensor system using the thermal gradient to accommodate for adverse thermal effects on the optical sensor.

According to an aspect of the invention, the method may include using a thermal imager to image the portion.

According to an aspect of the invention, the method may include using a processor to convert an image from the thermal imager into a thermal gradient map.

According to an aspect of the invention, the method may include using a microbolometer to determine a portion of the portion of the optical window that is opaque.

According to an aspect of the invention, the method may include marking a datum on the optical window and using a visible camera of the thermal imager to measure a change in position of the datum.

According to an aspect of the invention, the method may include projecting light on the portion of the optical window, determining a pattern of the light, and measuring deflections of the light to determine the thermal gradient.

According to an aspect of the invention, the method may include storing data regarding the thermal gradient in a memory and using the data to apply corrections to the optical elements of the sensor system if the thermal imager fails.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

The annexed drawings, which are not necessarily to scale, show various aspects of the invention.

DETAILED DESCRIPTION

The principles described herein may be suitable for any application implementing an optical window. An example of a suitable application may be a defense-type application or an aerospace application, but many other applications may be suitable. The thermal detection system and method described herein may be implemented in an airborne platform or vehicle such as a missile, aircraft, or spaceplane. Many other platforms and applications may be suitable, such as transparent armor or any application that implements transparent ceramic surfaces or conformal dome or window type structures. More specifically, the systems and methods as described herein may be arranged within an airborne body that includes an optical window and a sensor system contained within the airborne body. The thermal detection system may include a thermal imager for imaging a portion of the optical window and the portion may coincide with an optical path of a sensor of the sensor system. The system may include a processor that is in communication with the thermal imager for receiving images of the portion and determining a thermal gradient or temperature map of the portion. The system may further include an optical corrector that is in communication with the processor and uses the thermal gradient to apply corrections to optical elements of the sensor system. The system is advantageous in that the thermal gradient of the optical window is directly measured in real-time such that precise corrections are made to the optical elements of the sensor system to enable performance of the sensor system in spite of distortions along the optical paths of the sensor system. Thus, using the thermal imager to determine the thermal gradient may improve the performance of the sensor system as compared with using conventional methods that may not directly and accurately determine the thermal gradient in real-time.

Figure 1:
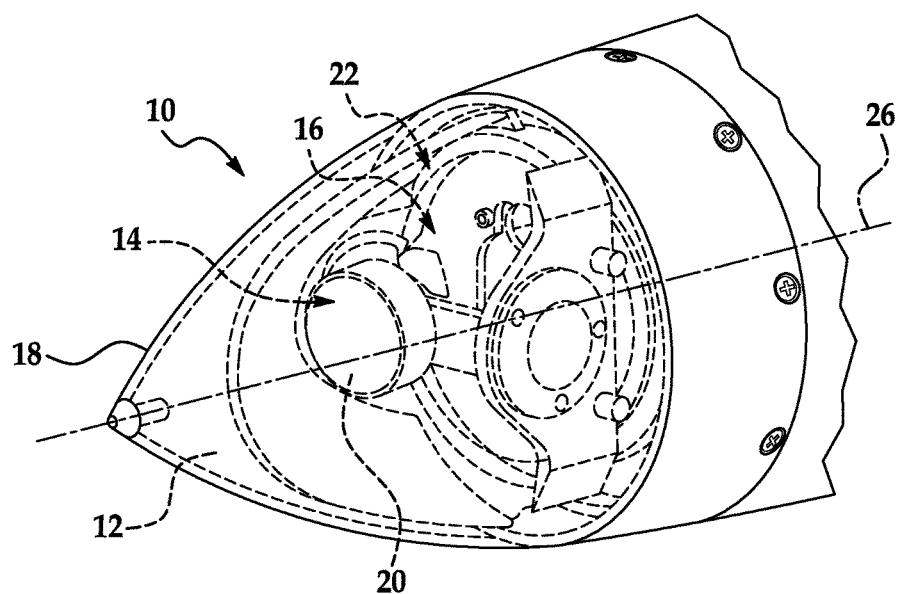
FIG. 1 is a drawing showing a sectional view of a radome having a sensor system and an optical window.

Referring now to FIG. 1, an exemplary airborne body 10 having a thermal detection system is shown. The airborne body 10 may be a spaceplane and the airborne body 10 may include an optical window 12. The optical window 12 may be a conformal, non-spherical dome, such as a radome that surrounds a sensor system 14. The sensor system 14 may include at least one electro-optical or infrared sensor 16 arranged within an interior surface 18 of the optical window 12. The optical window 12 may be formed of any suitable material such as a transparent ceramic material. The transparent ceramic material may have a transmissivity band in the mid-wave infrared spectrum or in the long-wave infrared spectrum. For example, the ceramic material may be a nanocomposite optical material having a transmissivity band in the long-wave infrared spectrum. Examples of suitable optical materials for the optical window 12 include barium fluoride, calcium fluoride, magnesium fluoride, fused silica, germanium, magnesium fluoride, potassium bromide, sapphire, silicon, sodium chloride, and zinc sulfide. Many other materials may be suitable.

The sensor system 14 may include a plurality of optical sensors that draw upon the electromagnetic spectrum and the sensor type may be dependent on the application of the airborne body 10. For example, the sensor system 14 may be configured for target acquisition and reconnaissance, surveillance, tracking, range-finding, laser designation, or any other suitable function. The sensor system 14 may be operable in a mid-wavelength infrared range or in a long-wavelength infrared range. The sensor system 14 may be operable in a short-wavelength infrared range. The sensor 16 may be a detector and the sensor system 14 may include receiver optics such as a lens 20 that is optically coupled to the sensor 16. The sensor system 14 may include a roll/nod seeker 22 positioned behind the optical window 12 for rotation around a roll axis that is coincident with an axis of symmetry 26 of the optical window 12

Figure 2:
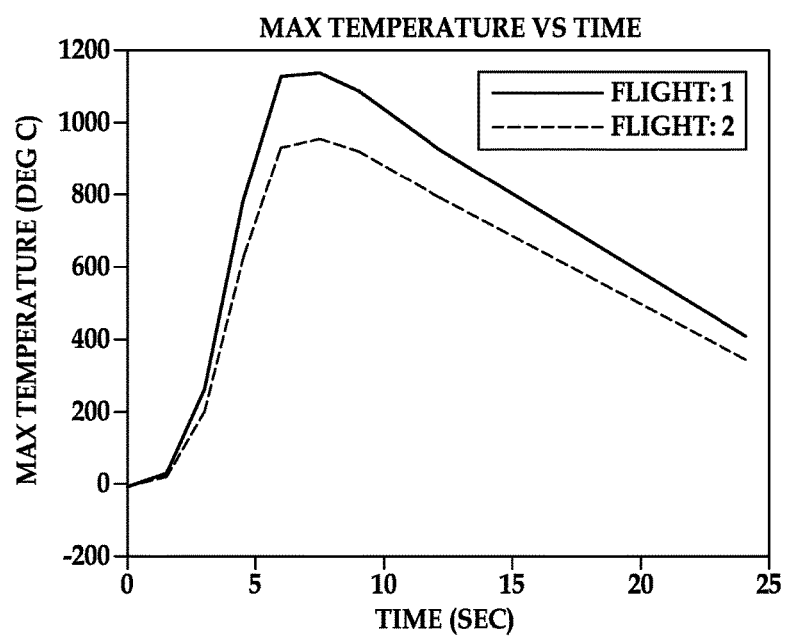
FIG. 2 is a graph showing the temperature of the radome of FIG. 1 as a function of time.
Figure 3:
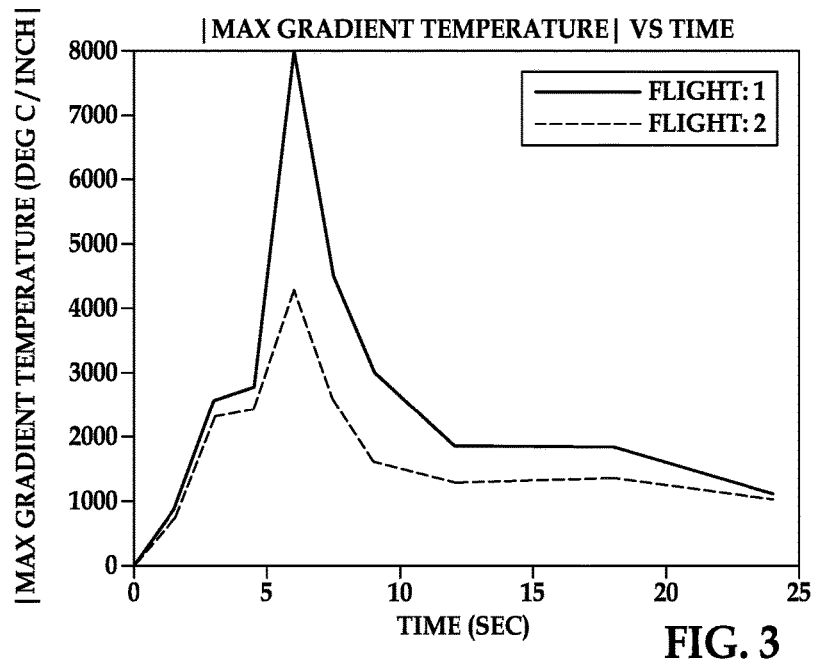
FIG. 3 is a graph showing a gradient temperature of the radome of FIG. 1 as a function of time.
Figure 4:
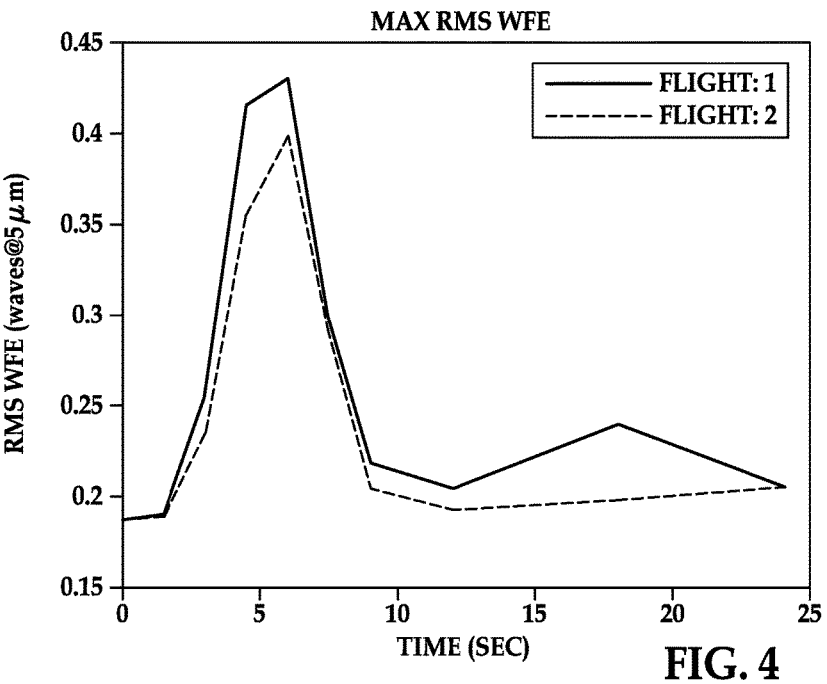
FIG. 4 is a graph showing the root-means-square wavefront error of the radome of FIG. 1 as a function of time.
Figure 5:
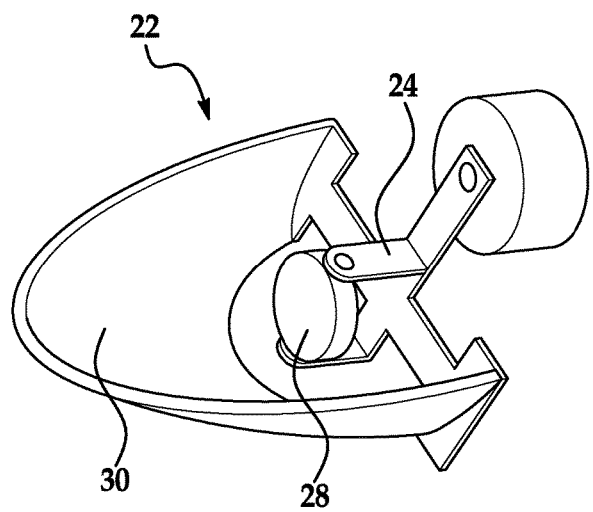
FIG. 5 is a drawing showing a sectional view of an optical corrector for the sensor system of FIG. 1.

FIGS. 2-4 are graphs that show the effects of aerothermal distortions of the optical window 12 during flight of the airborne body 10. Such distortions may impact performance of the sensor system 14 due to wavefront error. The graphs are shown for two different flight profiles of an exemplary airborne body or radome. FIG. 2 is a graph showing the temperature change of the airborne body, where the x-axis is elapsed time and the y-axis is the temperature. As shown in FIG. 2, the temperature of the optical window may change from zero degrees Celsius to over 1000 degrees Celsius in less than ten seconds. FIG. 3 is a graph showing the temperature gradient, where the x-axis is elapsed time and the y-axis is the temperature gradient measured in degrees Celsius per inch. As shown in FIG. 3, the temperature gradient of the optical window may increase from zero to approximately 8000 degrees Celsius per inch, or approximately 3150 degrees Celsius per centimeter, in approximately five seconds. FIG. 4 shows the wavefront error of the optical window, where the x-axis is elapsed time and the y-axis is the root-mean-square (RMS) wavefront error (WFE) measured in waves at five microns. As shown in FIG. 4, the wavefront error may increase from a fraction of 0.15 to 0.45 in approximately five seconds. The rapid temperature increase, temperature gradient increase and increase in the RMS WFE are generally produced across the window and the resulting thermal gradient may change an optical index of refraction and optical absorption coefficients of the window materials such that the normal paths of the optical rays may be distorted. Thus, the thermal distortion may cause a reduction in sensor performance and impact the normal vehicle functions Referring in addition to FIG. 5, the sensor system 14 may include optical elements and an optical corrector for applying corrections to the optical elements and accommodating for the aerothermal distortions shown in FIGS. 2-4. The optical elements may include a sensor that is part of an optical train. The sensor may receive radiated energy and converts the radiated energy to an electrical signal. The optical train may be fixed in orientation or mounted on a gimbal that rotates and allows sensing over a field of regard. For example, the optical elements of the sensor system 14 may include a roll/nod seeker 22 positioned behind the optical window 12 of FIG. 1. The roll/nod seeker 22 may include a roll gimbal 24 that rotates around a roll axis that me coincident with an axis of symmetry 26 (FIG. 1) of the optical window 12. The roll/nod seeker 22 may include a nod gimbal 28 on the roll gimbal 24 that rotates about a nod axis that is orthogonal to the roll axis at the gimbal center to point an optical axis in a multi-dimensional space defined by the axes. The receiver optics on the nod gimbal 28 may receive optical radiation in a field-of view along the optical axis. The receiver optics may include multiple lenses and mirrors. The seeker 22 may be configured to slew the field-of-view over a predetermined field-of-regard, such as a hemisphere. The sensor system 14 may further include an optical corrector or a transparent arch 30 having an optical corrector shape that is responsive to a shape of the optical window 12. The arch 30 may be mounted on the roll gimbal 24 within an optical path between the optical window 12 and the receiver optics as the seeker slews. The optical corrector may include half-arch, dual-arch, or multi-arch correctors and the arch or arches may have any suitable shape. For example, the arch or arches may be aspheric in shape.

The optical corrector may be used to correct the optical elements in response to the detected thermal gradient of the optical window 12. For example, the optical corrector may include a deformable mirror of the optical system. The deformable mirror may be programmed and deformed to a desired shape and a corrective shape to the mirror may be applied in response to the system information. The deformable mirror may alter the optical path length of the sensor by changing the distance a wavefront has travelled. Any suitable dynamic correcting element may be used and there may be many different types of optical correctors.

Figure 6:
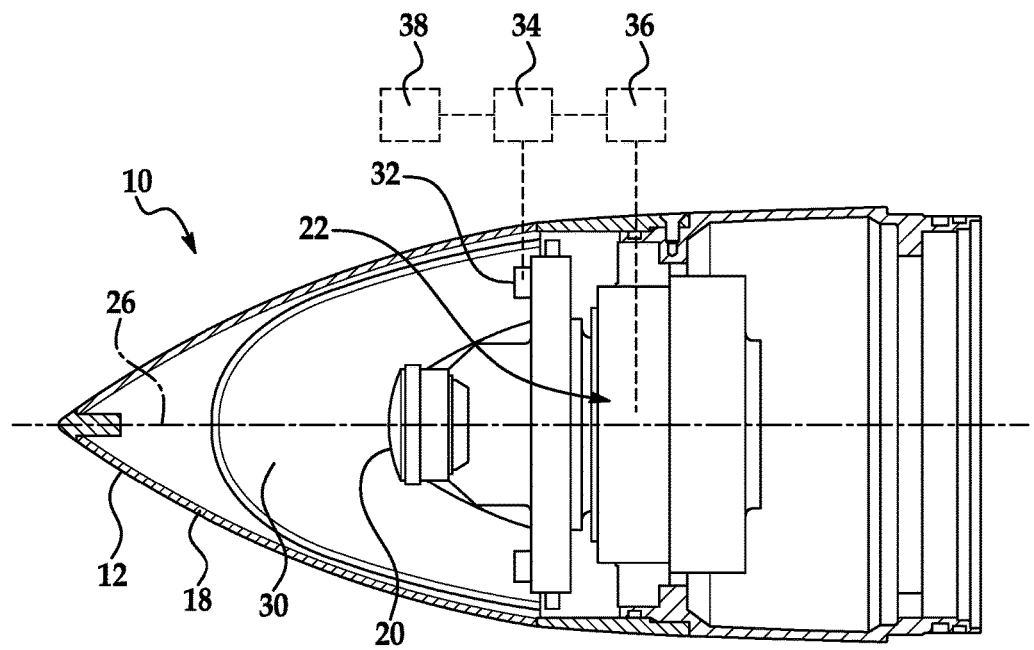
FIG. 6 is a drawing showing a sectional view of a system for detecting a thermal profile of the optical window of FIG. 1.

Referring now to FIG. 6, the airborne body 10 may include a thermal detection system that includes a thermal imager 32 for imaging a portion of the optical window 12 and the portion may coincide with an optical path of at least one of the sensors of the sensor system 14. The thermal detection system may be configured to detect or measure a thermal profile of the optical window 12. The thermal profile may include a set of time-temperature data that is associated with the measurement of thermal temperatures at various locations along the optical window 12. The thermal detection system may be configured to generate a map or plot of the data such that appropriate optical corrections may be made to accommodate for adverse thermal effects on the optical window 12. The thermal imager 32 may be arranged within the interior surface 18 of the radome or optical window 12. The thermal imager 32 may be two-dimensional and formed integrally with the sensor system 14. The thermal imager 32 may be mounted to an existing structural component of the sensor system 14, such as any suitable mount. The thermal imager 32 may be configured to image the portion of the interior surface 18 of the optical window 12 during flight of the airborne body and directly measure the temperature of the interior surface 18 over the field-of-regard. The thermal imager 32 may include any suitable thermal imaging camera and at least one sensor that is a separate component from the sensors of the sensor system 14. The thermal imager 32 may include a plurality of sensors. The sensor or plurality of sensors may be offset with respect to optical axes within the optical window 12. Arranging the sensors offset to the optical axes, such as offset from the optical axis of the lens 20, may be advantageous in that the thermal imager may be more easily integrated into the sensor system 14.

The thermal imager 32 may use a combination of different types of sensors. The sensor may be configured to sense or detect long-wave infrared or mid-wave infrared. In an exemplary embodiment, a thermal detector such as a bolometer may be used. The bolometer may be a microbolometer having a grid or array of vanadium oxide or amorphous silicon heat sensors located on a corresponding grid of silicon. Infrared radiation from a specific range of wavelengths may strike the grid and change the electrical resistance such that the resistance change is measured and converted into a temperature map. The microbolometer may be configured to determine where the optical window 12 is opaque. The thermal detection system may include a processor 34 and the microbolometer may be configured to send the data pertaining to the processor 34. The processor 34 may be configured to determine the thermal gradient and generate or produce a temperature map of the optical window 12. The processor 34 may include any suitable computer, hardware, software, or integrated circuit.

In another exemplary embodiment, the thermal imager 32 may include a visible camera. The optical window 12 may include a coating, marking or datum and the visible camera may be used to measure a change in position of the datum. The thermal imager 32 may be configured to send the data pertaining to the position of the datum to the processor 34 and the processor 34 may be configured to determine the thermal gradient or produce a temperature map of the optical window 12.

In still another exemplary embodiment of the thermal imager 32, the thermal imager 32 may include a light source to project light on the optical window 12 and determine a pattern of the light on the optical window. The thermal imager 32 may be configured to measure any deflections on the surface of the optical window 12 and the processor 34 may be configured to receive the data pertaining to the deflections to determine the temperature map of the optical window 12.

In still another exemplary embodiment, the sensor system 14 may include a long-wave infrared sensor that is operable for a function of the airborne body and the sensor may additionally be used to measure the temperature profile of the optical window 12. Using at least one sensor of the sensor system 14 of the airborne body to image the window may be advantageous in that additional sensors, other than the sensors of the airborne body's sensor system, may not be provided.

The thermal imager 32 may be in communication with the processor 34 and the processor 34 may receive images of the optical window 12 from the thermal imager 32. The processor 34 may be configured to produce any suitable temperature map. For example, the temperature map may be a thermal gradient map of a thermal gradient across the window. The processor 34 may be configured to calculate the RMS wavefront error from the temperature map. The processor 34 may further include correction logic. The temperature map and the wavefront error may be fed to the correction logic in real time such that the correction logic may be used to determine the appropriate movement of the optical corrector to accommodate for the wavefront error. The processor 34 may be in communication with a controller 36 and the controller 36 may be in communication with the optical corrector or the arch 30 for controlling movement of the optical corrector in response to the real-time temperature map. The optical corrector may be used to accommodate for any optical aberrations of the sensor system 14, such as defocus, astigmatism, coma, or degradation. The optical corrector may be configured to correct the deformations of the incoming wavefront by deforming a mirror of the receiver optics of the sensor system 14.

The processor 34 may also include a memory 38 or a memory 38 may be provided as a separate component. The memory 38 may be used to store a lookup table that has predetermined corrections for a certain temperature map. The processor 34 may send data pertaining to the thermal images and temperature map of the optical window to the memory 38, such that the data may be used to continuously update the lookup table. The processor may also be configured to receive other data about the airborne body including flight altitude, speed of the airborne body, and environmental conditions. Data pertaining to many other parameters of the airborne body may also be detected and stored in the memory 38. The lookup table may then be used to allow predictions of the thermal gradient of the optical window 12 and apply corrections to the optical system based on receiving information about the other parameters of the airborne body. For example, the lookup table may be used in a future mission or flight of the airborne body and the corrections and thermal gradient may be determined based on the data in the lookup table.

Figure 7:
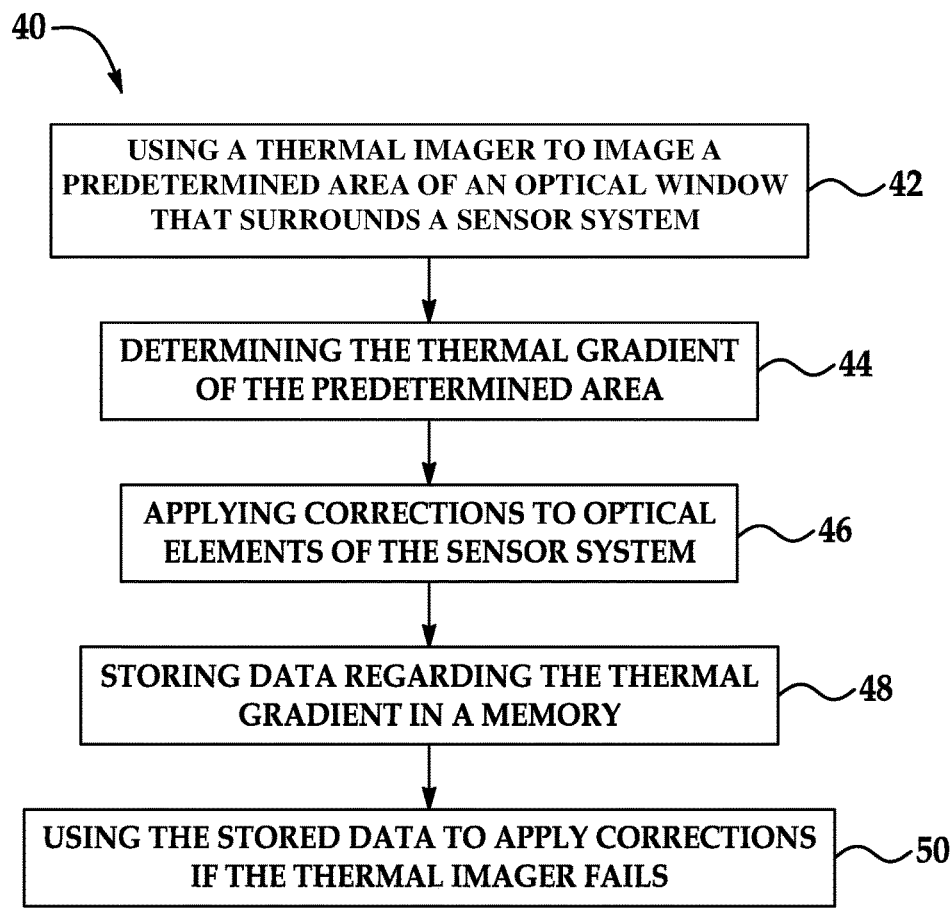
FIG. 7 is a flowchart illustrating a method for detecting the thermal profile of the optical window of FIG. 1.

Referring in addition to FIG. 7, a method 40 for detecting the thermal profile of the optical window 12 (FIG. 1) is schematically illustrated. Step 42 of the method 40 may include using the thermal imager 32 (FIG. 6) to image a portion of the optical window 12 that coincides with an optical path of the sensor system 14 (FIG. 1). After the thermal imager 32 has obtained images of the portion, step 44 may include determining the thermal gradient of the portion via the processor 34 (FIG. 6). Step 44 may further include using the processor 34 to determine the thermal gradient after receiving the thermal images from the thermal imager 32. The processor 34 may use the images from the thermal imager 32 to determine at what rate the temperature changes the most rapidly around the portion of the optical window 12 or any other particular location on the window.

The thermal gradient may be measured in kelvin per meter. The processor 34 may be configured to generate a thermal gradient map of the window 12.

After the thermal gradient is determined or the thermal gradient map of the window 12 is determined, step 46 may include applying corrections to optical elements of the sensor system 14. Corrections may be applied using any suitable corrector. After the thermal gradient is determined, step 48 may include storing data regarding the thermal gradient in the memory 38 (FIG. 6). In the event that the thermal imager 32 fails, step 50 may include using the stored data to apply corrections to the optical system based on the stored data.

Using the thermal imager is advantageous in that the temperature is directly detected in real-time. Another advantage is that the optical window may not be instrumented, such as a thermocouple that is integrated in the window, making the structure of the window more complex. Still another advantage is that the thermal imager enables correction of low-order and high-order aberrations for advanced conformal windows.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (external components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A thermal detection system for detecting a thermal profile of an optical window of an airborne body that contains a sensor system having optical elements, the thermal detection system comprising:
   a thermal imager arranged within the airborne body that images a portion of the optical window, wherein the portion of the optical window coincides with an optical path of the sensor system; and
   a processor that is in communication with the thermal imager and receives images of the portion of the optical window to determine a thermal gradient of the portion of the optical window, wherein the processor is configured to apply corrections to the optical elements of the sensor system.

2. The thermal detection system of claim 1, wherein the thermal imager includes a mid-wave infrared sensor or a long-wave infrared sensor.

3. The thermal detection system of claim 1, wherein the thermal imager includes a microbolometer.

4. The thermal detection system of claim 1, wherein the thermal imager includes a visible camera.

5. The optical system of claim 1, wherein the thermal imager includes a microbolometer.

6. The optical system of claim 1, wherein the thermal imager includes a visible camera.

7. The optical system of claim 1, wherein the thermal imager includes a long-wave infrared sensor.

8. The optical system of claim 1, wherein the optical window is a radome or a conformal dome.

9. The method of claim 1 further comprising using a microbolometer to determine a portion of the optical window that is opaque.

10. The method of claim 1 further comprising:
marking a datum on the optical window; and
using a visible camera of the thermal imager to measure a change in position of the datum.

11. The method of claim 1 further comprising:
projecting light on the portion of the optical window;
determining a pattern of the light; and
measuring deflections of the light to determine the thermal gradient.

12. The method of claim 1 further comprising:
storing data regarding the thermal gradient in a memory;
using the data to apply corrections to the optical elements of the sensor system if the thermal imager fails.

13. An optical system located in an airborne body, the optical system comprising:
an optical window;
an optical sensor that is operable along an optical axis;
a thermal imager that images an interior area of the optical window, wherein the interior area coincides with the optical axis;
a processor that is in communication with the thermal imager and receives images of the interior area to determine a thermal gradient of the predetermined interior area; and
an optical corrector that is in communication with the processor and uses the thermal gradient to apply corrections to the optical sensor to accommodate for adverse thermal effects on the optical sensor.

14. The optical system of claim 13, wherein the thermal imager is arranged offset to the optical axis of the optical sensor.

15. The optical system of claim 13, wherein the optical window is formed of a transparent material having a transmissivity band in a mid-wave infrared range.

16. The optical system of claim 13, wherein the optical window is formed of an opaque material having a transmissivity band in a long-wave infrared range.

17. The optical system of claim 13, wherein the optical sensor is a long-wave infrared sensor and the long-wave infrared sensor may be used as the thermal imager.

18. The method of claim 17 further comprising using a thermal imager to image the portion.

19. The method of claim 18 further comprising using a processor to convert an image from the thermal imager into a thermal gradient map.

20. A method for detecting a thermal profile of an optical window located on an airborne vehicle that contains a sensor system, the method comprising:
imaging a portion of the optical window that coincides with an optical path of the sensor system;
determining the thermal gradient of the portion of the optical window; and
applying corrections to optical elements of the sensor system using the thermal gradient to accommodate for adverse thermal effects on the optical sensor.

\* \* \* \* \*